(12) United States Patent
Matsumoto et al.

(10) Patent No.: US 7,549,180 B2
(45) Date of Patent: Jun. 23, 2009

(54) OPTICAL STRUCTURE FOR EYES

(75) Inventors: Kimio Matsumoto, Higashiosaka (JP); Noriaki Atake, Higashiosaka (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 184 days.

(21) Appl. No.: 11/291,375

(22) Filed: Nov. 30, 2005

(65) Prior Publication Data
US 2006/0119948 A1 Jun. 8, 2006

(30) Foreign Application Priority Data
Nov. 30, 2004 (JP) ............... 2004-347776

(51) Int. Cl.
*A61F 6/02* (2006.01)
(52) U.S. Cl. .......................................... 2/436
(58) Field of Classification Search .............. 2/6.3, 2/434–436
See application file for complete search history.

(56) References Cited

U.S. PATENT DOCUMENTS

| | | | |
|---|---|---|---|
| 5,018,223 A * | 5/1991 | Dawson et al. ............ | 2/436 |
| 5,845,342 A * | 12/1998 | Park ........................... | 2/424 |
| 6,601,240 B2 * | 8/2003 | Tsubooka .................... | 2/436 |
| 6,611,966 B1 * | 9/2003 | Yamamoto et al. .......... | 2/436 |
| 6,772,448 B1 * | 8/2004 | Hockaday et al. ........... | 2/435 |

FOREIGN PATENT DOCUMENTS

| JP | 61-233701 | 10/1986 |
|---|---|---|
| JP | 03-064730 | 3/1991 |

* cited by examiner

*Primary Examiner*—Katherine Moran
(74) *Attorney, Agent, or Firm*—William L. Androlia; H. Henry Koda (57) ABSTRACT

An optical structure for eye, for example, ski goggles, has an outer lens and an inner lens disposed in parallel. A peripheral sealing is provided between and along the entire circumferential edges and their surroundings between the lenses. Between the lenses is a room defined by the rear face of the outer lens and the front face of the inner lens and an inorganic film is provided on the rear face of the outer lens and/or the front face of the inner lens. The inorganic film is prevented from peeling of due to external factors.

39 Claims, 7 Drawing Sheets

Front ⟷ Rear

Front ←→ Rear

Fig. 7

Front ←→ Rear

Fig. 8

OPTICAL STRUCTURE FOR EYES

FIELD OF THE INVENTION

The present invention relates to an optical structure for eyes such as eye-glasses, ski goggles, goggles for driving vehicles, light-shielding goggles, face guards for emergency, and light shielding face guards.

PRIOR ART

A typical optical structure for eyes is composed of double lenses or triple lenses, the outside lens of which has an inorganic film on its outer front face with a process such as a mirror process and an antireflection film process.

The foregoing inorganic film however might peel off due to various external factors such as (1) flying articles, wiping flaws and unwanted contact when a user falls down, (2) direct exposure to moisture such as snow and rain, and (3) direct exposure to ultraviolet light.

An example of a known method for solving the problem is disclosed in Japanese Patent Application Laid-Open No. 61-233701 (FIG. 1). This teaches reducing flaws and invasion of moisture by coating a low fictional substance such as fluorine or silicone over the surface of the inorganic film. However, fluorine and silicone coatings are likely to peel off and the effect of them does not last long.

SUMMARY OF THE INVENTION

It is hence an object of the present invention to provide an optical structure for eyes in which an inorganic film is prevented from peeling off from a lens due to external factors.

The optical structure for eyes of the present invention includes an outer lens and an inner lens disposed in parallel. A peripheral seal is given along and between the respective entire circumferential edges or their surroundings of the outer and inner lenses to form a room. An inorganic film is applied on at least one of the rear face of the outer lens and the front face of the inner lens that define the room.

The outer and inner lenses may be composed of resins such as polycarbonate base, polyester base, polyamide base, acryl base, cyclic olefin base, cellulose group base, polysulfone base, polyphenylene sulfide base, vinyl chloride base and polystyrene base resins and a transparent alloy resin thereof, and further, may be composed of thermosetting resin such as urethane base, polyepoxy base, acryl base and allyl base resins. From the viewpoint of toughness, a polycarbonate base thermoplastic resin and a urethane base thermosetting resin are preferable.

The thickness of a lens is 0.3 to 10 mm and preferably 0.5 to 7 mm considering strength and processability.

The peripheral seal is given along and between the respective entire circumferential edges and/or their surrounding of the outer and inner lenses in order to prevent water invasion into the room between the lenses.

The inorganic film is a thin film made of such as metal, metal oxide containing silicon and metal nitride containing silicon. The thin film is generally formed under high vacuum by a vacuum deposition method, a spattering method and the like, and has a thickness of 0.5 mm or less per layer. The thin film may be applied over a lens either before or after being punched out, or either before or after being bent.

The inorganic film is provided on the lens face defining the room in order to prevent the film from peeling by contact with water, eliminate abrasion of the film by contact with a user's hand and etching and keep the performance and appearance that the lens inherently has.

A conventional optic structure has an inorganic film on the front face of the outer lens and sometimes has a silicone or fluorine coating is further added thereon for preventing the peeling of the inorganic film. However on the coating face, printing cannot be added. On the other hand, in the present invention, since the inorganic film is applied on at least one of the rear face of the outer lens and the front face of the inner lens, a fluorine or silicone coating on the front face of the outer lens becomes unnecessary from the viewpoint of preventing the peeling of the inorganic film and printing can be added on the front face of the outer lens.

In the optical structure for eyes of the present invention, an inorganic film applied on the front face of the inner lens is a metal film.

Since the metal film functions as a metal glorious film (a miller film) viewed from a bright side and a semi-transparent film viewed from a dark side, using a metal film is advisable for an optical processing method from the viewpoint of light shielding performance.

In the present invention, being provided on the front face of the inner lens, the metal film can be prevented from peeling by water, abrading by contact with a user's hand and etching and the lens keeps its inherent performance and appearance. The metal film is generally provided on the lens with a vacuum deposition method or a spattering method, and the metal includes gold, silver, chromium, nickel, tin and aluminum.

The metal film is in general applied on a lens substrate before or after being punched out into a lens shape with the vacuum deposition method. Alternatively, the metal film may be added on a functional film such as a hard coat film.

In particular, when bending a flat lens on which a metal film has been firstly applied, bending it with the metal film inside generates crumples in the film and peeling of the film. When the lens is bent with the metal film outside, the lens with the film on the convex face is advisable to be provided as the inner lens in which the film is present on the front face of the inner lens.

In the optical structure for eyes of the present invention, the inorganic film applied on the rear face of the outer lens is an antireflection film.

The antireflection film prevents dazzling of the lens viewed from outside, and increases the amount of transmission light of the lens viewed from inside so that a user can enjoy the bright view. When bending a flat lens on which a metal film has been firstly applied, the lens having the metal film on its convex face is advisable to be used as the inner lens and the antireflection film is advisable to be applied on a concave face of the outer lens.

The antireflection film is in general applied with a vacuum deposition method or a spattering method so as to provide a multilayered inorganic oxide film. A layer composition and a thickness can be theoretically determined depending on adhering property with a lens substrate, the refractive indices of the lens substrate and the inorganic oxide and antireflection performance.

When the outer lens is immersed in a hard coat solution and both the faces are treated therewith, the antireflection film may be provided on the hard-coated concave face of the outer lens.

In the optical structure for eyes of the present invention, at least the outer lens may be provided with an ultraviolet absorption function or an ultraviolet reflection function.

It is preferable to cut nearly 100% of ultraviolet light with a wavelength of 400 nm or less. For this purpose, compounding ultraviolet absorbent and/or dye in lens forming resins, providing an inorganic film reflecting ultraviolet rays on the front face of the outer lens, and a combination thereof can be employed.

The optical structure for eyes of the present invention may be provided with an antifogging film on the rear face of the inner lens. The rear face of the inner lens, which faces a wearer's eyes, is likely to be fogged by moisture, but this is prevented by the antifogging film.

The antifogging film is made mainly of hydrophilic polymer and surfactant. An antifogging liquid may be coated on one side of a film or flat sheet with a roll coater or a lens may be immersed in an antifogging liquid to have coating on both faces. When the adhering property between the antifogging film and the metal film is poor, it may be preferable to provide the antifogging film after providing the metal film on the front face of the inner lens.

The whole peripheral sealing is made up of water cut-off buffer material. The water cut-off buffer material is composed of resin having elasticity, flexibility and waterproof property. The waterproof property herein means properties not to dissolve and swell in water and not to let water pass through.

The water cut-off buffer material is composed of natural rubber base, synthetic rubber base, polyurethane base, polyolefin base, polyester base, polyamide base, polysulfone base, polyphenylene sulfide base, vinyl chloride base, polystyrene base, cellulose base resins or substances and polymer alloy resin thereof. Any of them may contain closed cells, but in such a case, a polyolefin base or polyurethane base resin is preferable, especially in elasticity, flexibility and waterproof property.

The thickness of the water cut-off buffer material is 0.4 to 10 mm and preferably 1 to 6 mm. The thickness of 0.4 mm or less may cause unwanted contact between the outer and inner lenses, while the thickness exceeding 10 mm, resulting in a thick optical structure, may lose an good appearance of the lens. In order to adhere the lens and the water cut-off buffer material, an adhesive for resin having an appropriate waterproof property is coated between the buffer material and the lens, or a double-sided adhesive tape or sheet having an appropriate waterproof property is used therebetween.

The optical structure for eyes of the present invention may be provided with a pressure adjusting hole in the outer lens, the inner lens or/and the cut-off buffer material so as not to generate difference between the inner pressure of the room and atmospheric pressures.

The pressure adjusting hole makes the inner pressure of the room similar to an external pressure to prevent swelling and shrinking of the room depending on changes of atmospheric pressures. The hole with a diameter of about 0.1 to 0.5 mm is provided on at least one of the outer lens, the inner lens, and the cut-off buffer material. The pressure adjusting hole of 0.1 mm diameter is poor in effect and that of 5 mm or more diameter loses a good appearance.

In the optical structure for eyes of the present invention, the pressure adjusting hole is covered with a water-proof filter having air permeability.

The water-proof filter has air permeability for preventing water, snow and ice from invading into the room through the pressure adjusting hole and equalizing the inner pressure of the room to outside air pressure. Those having such permeability include the stretched film of fluorine resin called as GOATEX (trade mark), a polyurethane film and the like. A cloth laminating or coating such a film is provided as a filter over the pressure adjusting hole.

For the purpose of providing the water-proof filter to a lens, a double-sided adhesive tape or sheet having waterproof property is convenient. In that case, the adhesive agent of the tape or sheet should not be positioned at the portion corresponding to the pressure adjusting hole.

The optical structure for eyes of the present invention includes an outer lens, a middle lens and an inner lens in parallel. A peripheral seal is given along and between the respective entire circumferential edges and/or their surroundings of the outer and middle lenses to form a front room therebetween, and along and between the respective entire circumferential edges and/or their surroundings of the middle and inner lenses to form a rear room therebetween. An inorganic film is given on at least one of the rear face of the outer lens and the front face of the middle lens that define the first room and the rear face of the middle lens and the front face of the inner lens that define the rear room. The lens, the peripheral seal and the inorganic film are basically as described above.

In the optical structure for eyes of the present invention, the inorganic film provided on the front face of the middle lens and/or the front face of the inner lens is a metal film. The metal film is basically as stated above. When bending the lens with the metal film outside, the lens is desirable to be used as the middle lens and/or the inner lens having the metal film on the convex face, or the front face.

In the optical structure for eyes of the present invention, the inorganic film provided on the rear face or faces of the outer lens and/or the middle lens is an antireflection film. The antireflection film is as described above.

In the optical structure for eyes of the present invention, at least the outer lens may have an ultraviolet absorption function or an ultraviolet reflection function. The ultraviolet absorption function and the ultraviolet reflection function are as described above.

The optical structure for eyes of the present invention is provided with a hard coat film on the front face of the outer lens. The hard coat film is preferably provided on the front face of the outer lens which is most subject to external damage. The material of the hard coat film is acryl base or silane base. From the viewpoint of surface hardness and easiness of coating, in general, those mainly contain hydrolyzed substance of a silane base compound and inorganic sol particles such as silica sol are preferable.

The hard coat film may be provided on one side or both sides of the lens. For providing the film on one side, hard coat liquid is coated on one side of a film or flat sheet with a roll coater and cured. For providing the film on both sides, a flat or bent lens is immersed in hard coat liquid and after the lens being taken out therefrom, the remained liquid on the lens is cured. Fluorine base or silicon base water and/or oil repellent treatment on the hard coat film of the front face of the outer lens prevents water drops, snow and ice from adhering to the lens and allows to simply wipe out soil of a user's hand and oil stain. From the viewpoint of durability, water and/or oil repellent treatment may be preferably provided with a fluorine base silane compound on the hard coat film by a vacuum deposition method or an immersion method.

The optical structure for eyes of the present invention is provided with an antifogging film on the rear face of the inner lens. The antifogging film is as described above.

In the optical structure for eyes of the present invention, the peripheral seal is made up of water cut-off buffer material. The water cut-off buffer material is as described above.

The optical structure for eyes of the present invention is provided with a pressure adjusting hole in the outer lens, the middle lens, the inner lens or/and the water cut-off buffer material not to generate difference between the inner pressures of the front and rear rooms and atmospheric pressures. The pressure adjusting hole is as described above.

In the optical structure for eyes of the present invention, the pressure adjusting hole is covered with a water cut-off filter having air permeability. The water cut-off filter is as described above.

According to the optical structure for eyes of the present invention, the peeling of an inorganic film due to external factors unlikely happens.

DESCRIPTION OF THE PREFERRED EMBODIMENTS

A first embodiment is illustrated in FIGS. 1 to 5 as the best mode for carrying out the optical structure for eyes of the present invention.

Figure 1:
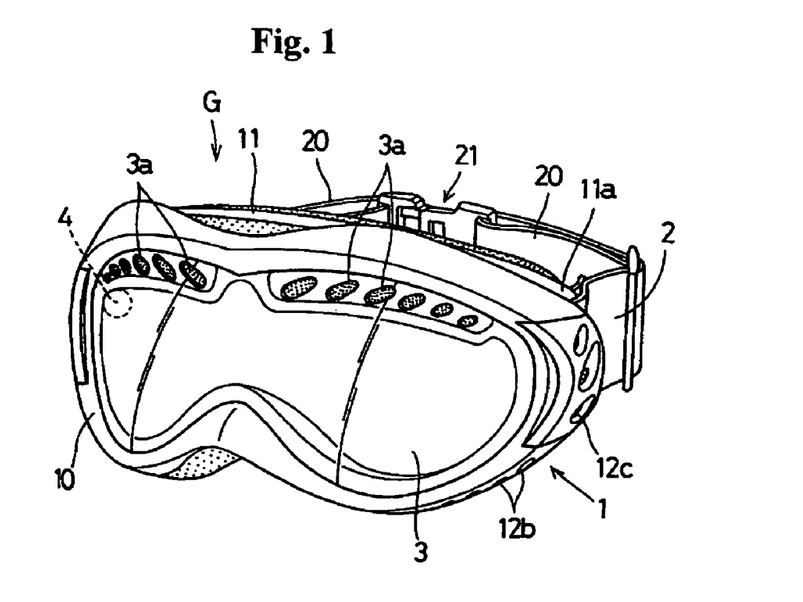
FIG. 1 is a perspective view of a double-lens-type ski goggle as an optical structure for eyes of a first embodiment of the present invention.
Figure 2:
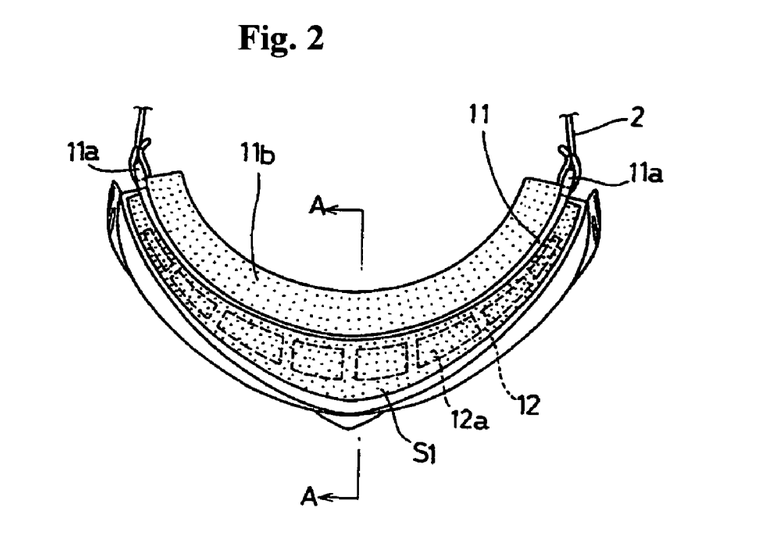
FIG. 2 is an upper view of the goggle.

As shown in FIGS. 1 and 2, a ski goggle G includes a goggle frame 1, an elastic band 2 linked with the goggle frame 1, a goggle lens 3 detachably fitted in the goggle frame 1, and a water cut-off filter 4 provided on the goggle lens 3.

Figure 3:
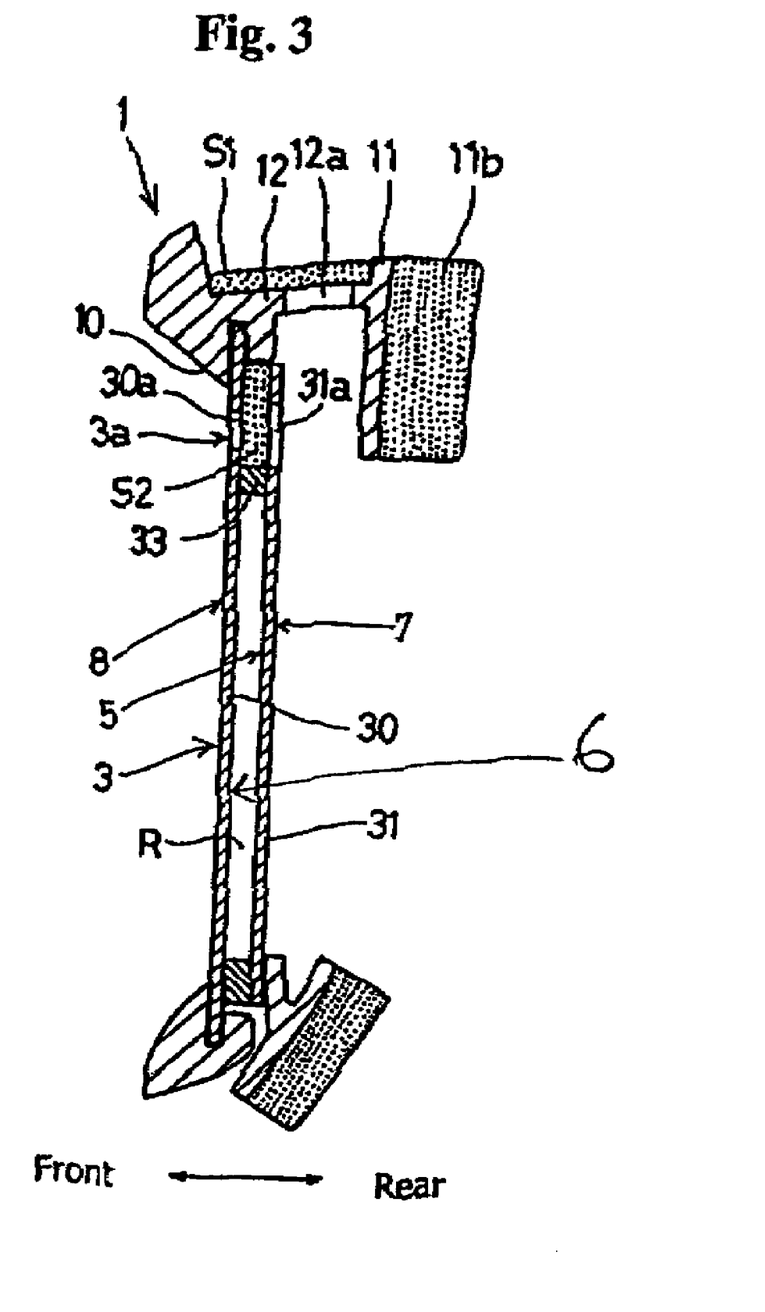
FIG. 3 is a sectional view taken at line A-A in FIG. 2.

The goggle frame 1 is made up of soft material such as elastic synthetic resin, rubber and the like. As shown in FIGS. 1 and 3, the frame 1 has a lens fitting rim 10, a facial seat 11, and a peripheral wall portion 12 linking the lens fitting rim 10 with the facial seat 11. The goggle lens 3 is detachably fitted in the lens fitting rim 10.

As shown in FIGS. 2 and 3, both ends of the facial seat 11 have connection portions 11a with holes for connecting the elastic band 2. A contact member 11b made of such as sponge and montplane is attached to the facial seat 11 to provide a comfortable fitting with a wearer's face.

As shown in FIGS. 1 and 3, the peripheral wall portion 12 has top and bottom composing walls and left and right composing walls. The top, bottom, left and right composing walls respectively have ventilations 12a, 12b and 12c, and these ventilations are covered with a thin sponge plate S1. Closing the ventilations with the sponge plate prevents snow and dusts other than air from invading into the inside of the goggle.

The elastic band 2 includes band bodies 20 and 20 that are designed to be elastic. The band bodies 20 and 20 respectively attached on the connection parts 11a and 11a are linked together by mean of a buckle 21.

Figure 5:
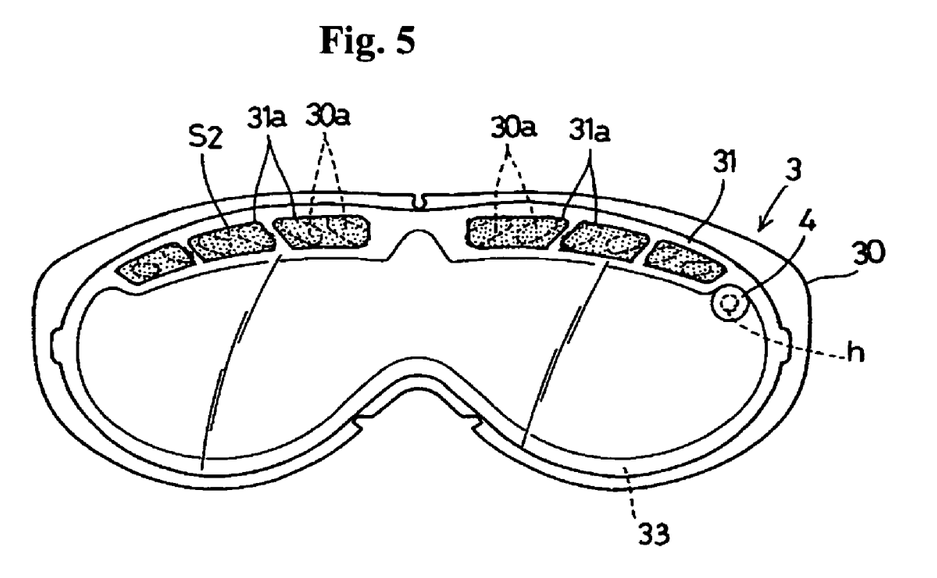
FIG. 5 illustrates a goggle lens used for the goggle viewed from the inner lens side.

As shown in FIGS. 3 and 5, the goggle lens 3 includes two lenses (i.e. an outer lens 30 and an inner lens 31) of transparent resin, and a water cut-off buffer material 33 for sealing between the entire circumferential edges of the two lenses.

The lenses 30 and 31 and the water cut-off buffer material 33 are fixed together with a double-sided adhesive tape. The two lenses 30 and 31 are disposed in parallel with 2 mm distance and the room R therebetween functions as an adiabatic layer. The outer and inner lenses 30 and 31 respectively have a thickness of about 0.6 mm and a convex shape in which the central portion protrudes from both end portions.

The outer lens 30 has holes 30a for a ventilation portion 3a near its upper edge and an outer peripheral rim as a portion to be fitted into the lens fitting rim 10 of the goggle frame 1.

The inner lens 31 is a little smaller in size than the outer lens 30, and has holes 31a for the ventilation portion 3a near its upper edge.

The outer lens 30 has an ultraviolet absorption function or an ultraviolet reflection function in order to cut most of ultraviolet rays. The front face of the outer lens 30 has a hard coat 8.

The front face of the inner lens 30 is applied with a metal film (an inorganic film) 5 of such as silver and chromium, and resulting in a mirror film viewed from a bright side and being semi-transparent viewed from a dark side. An antifogging film 7 is further added on the rear face of the inner lens 31.

Between the outer and inner lenses 30 and 31 is a sponge plate S2 provided at portions corresponded to the holes 30a and 31a for the similar reason why the sponge plate S1 is provided.

Figure 4:
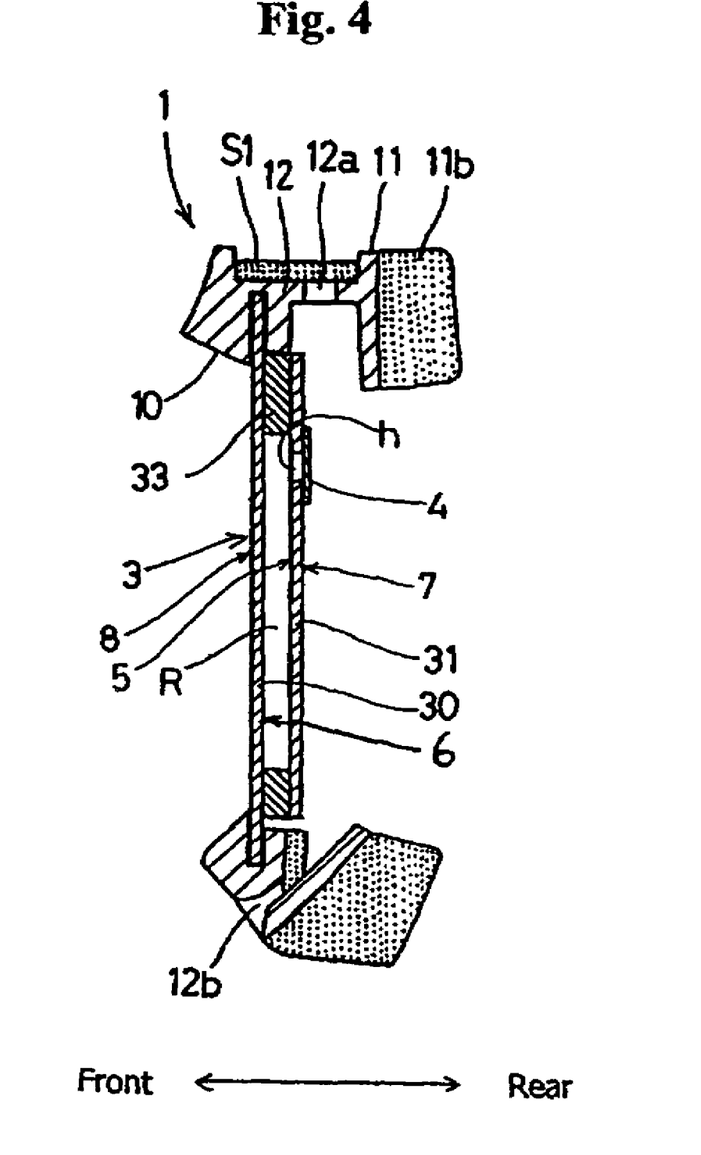
FIG. 4 is a sectional view of the goggle cut vertically at a part where a water cut-off filter is pasted.

As shown in FIGS. 4 and 5, the goggle lens 3 has a pressure adjusting hole h at a portion near its outer edge and off a wearer's visual field. The pressure adjusting hole h is covered with a water cut-off filter 4.

As the water cut-off filter 4, a water repellent permeation sheet is employed. This sheet prevents water from passing through buts allows air to pass through. The water repellent permeation sheet is obtained by pasting a continuous air hole porous material, for example, a tetrafluorinated ethylene resin textile layer, on a substrate with permeability in sheet form such as nylon cloth. The tetrafluorinated ethylene resin textile layer, after being stretched, becomes very tough and elastic and has a fine textile structure. Further it has many continuous air holes and a strong water repellent property. The average diameter of the holes is 0.2 to 5.0 μm, an air hole rate is 25 to 95%, and an air flow rate is 0.1 to 3000 (488 in $H_2O$) cc/sin/$in^2$.

When atmospheric pressure changes while downhill skiing and the like, the pressures inside and outside of the goggle lens 3 are equalized through the water cut-off filter 4, which therefore prevents deformation of the outer and inner lenses 30 and 31 and distortion of visual field.

When external atmospheric pressure increases, external air is sucked in from the pressure adjusting hole h1 through the water repellent permeation sheet. If a large quantity of moisture is contained in the external air, or even if snow and the like adhere on the outer face of a permeable substrate, with the above-mentioned water repellent permeation sheet, the invasion of moisture into the inside of the goggle lens 3 can be prevented. Nevertheless the goggle lens 3 has the pressure adjusting hole h1, fog is not generated inside of the goggle lens 3.

The benefits of the goggle described above are as follows.

(1) The metal film 5, or the inorganic film, is applied on the front face of the inner lens 31. Namely, the inorganic film does not exist on the front face of the outer lens 30 which is likely to have external contacts with flying articles, wiping scratches and damage when a wearer falls down. Therefore, the inorganic film of this goggle does not peel off by external factors.

(2) The outer lens 30 has an ultraviolet absorption function or an ultraviolet reflection function for cutting most of ultraviolet rays, and therefore the metal film 5 (i.e. the inorganic film on the front face of the inner lens 31) is not exposed to ultraviolet rays. As a result, the inorganic film of the goggle does not peel of by external factors.

(3) As described above, the metal film 5 or the inorganic film is applied on the front face of the inner lens 32. The water cut-off filter 4 prevents snow and moisture such as rain from invading into the room defined by the rear face of the outer lens 30 and the front face of the inner lens 31. The inorganic film is not directly exposed to moisture, and therefore it does not peel off by moisture.

(4) When a colored lens is employed as the outer lens 30, mirror process on the rear face of the outer lens 30 changes the color of the lens. On the other hand, the mirror process on the front face of the inner lens 31 does not change the color of the outer lens.

Some modifications of the first embodiment, which have the basic structure as a goggle similar to the first embodiment, are described below.

(1) The antireflection film, or the inorganic film, may be applied on the rear face of the outer lens 30 of the foregoing first embodiment. This antireflection film 6 or this inorganic film similarly does not peel off by external factors.

(2) The outer lens 30 of the first embodiment may be an ultraviolet absorbing polarized lens.

(3) Different from the first embodiment, the metal film 5, or the inorganic film, is applied on the rear face of the outer lens 30, not on the front face of the inner lens 31.

Figure 6:
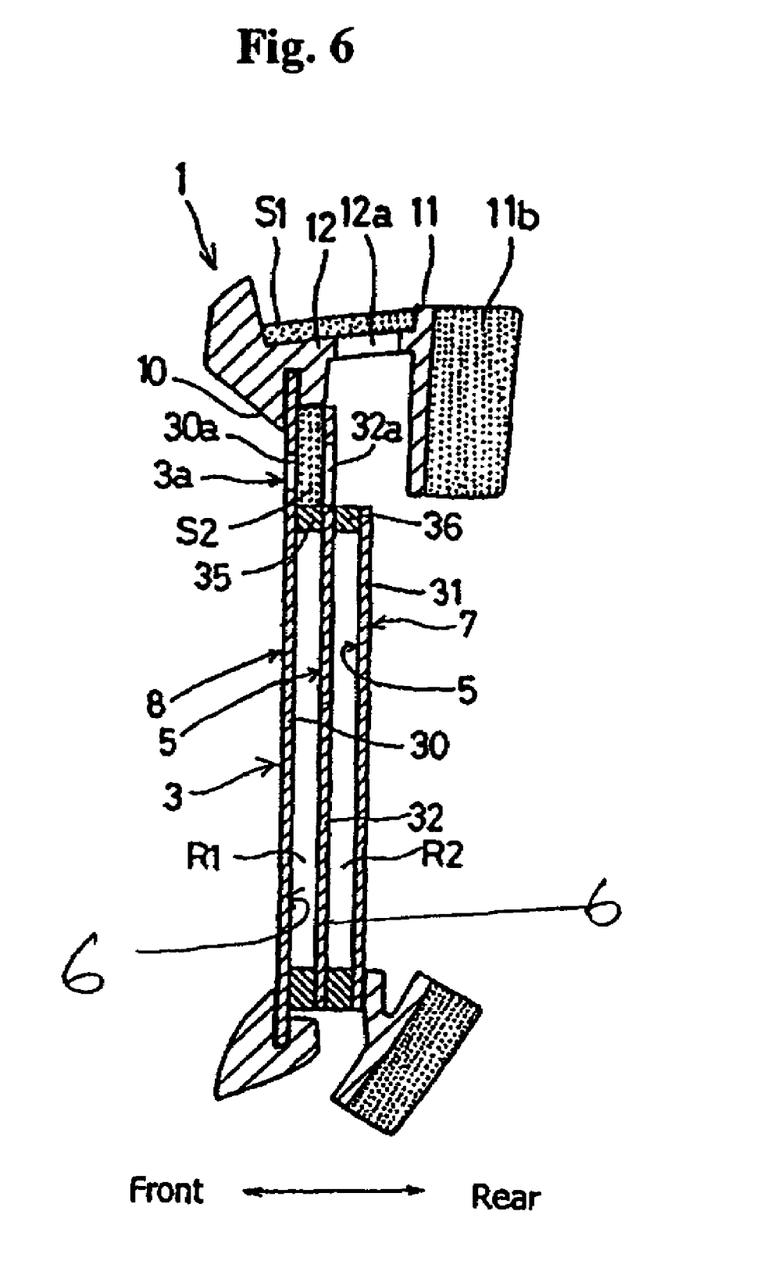
FIG. 6 is a sectional view of a triple-lens-type ski goggle as an optical structure for eyes of a second embodiment of the present invention, in which a ventilation portion and the like are cut vertically.
Figure 7:
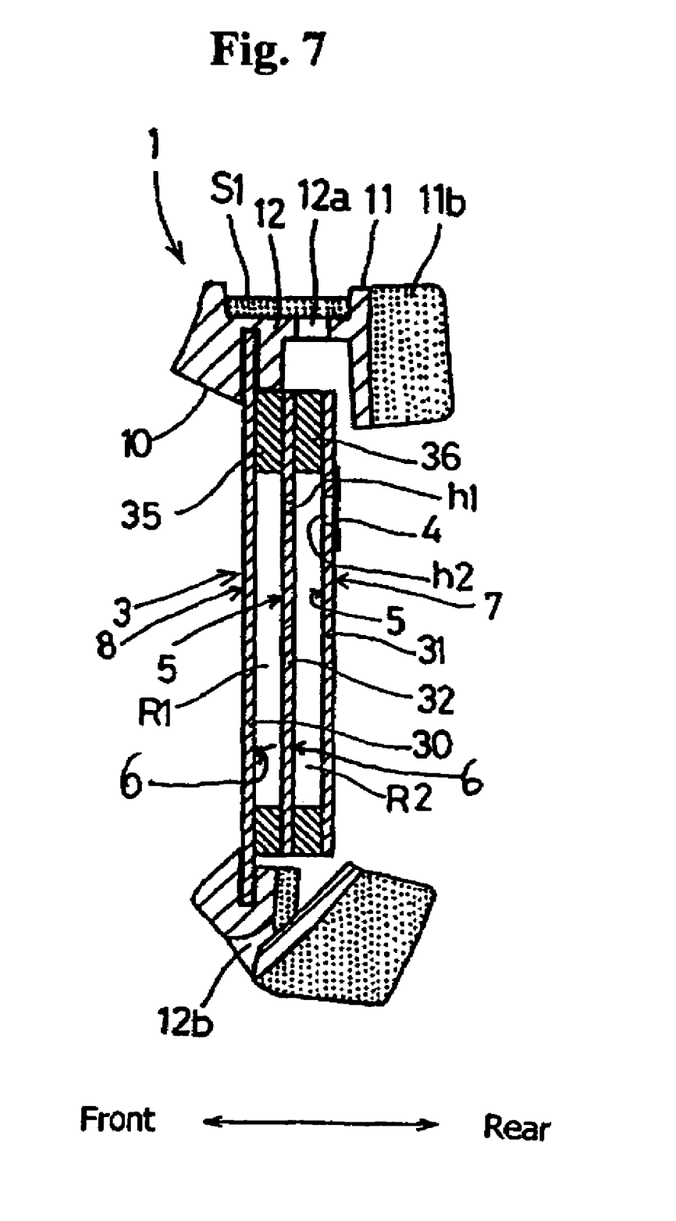
FIG. 7 is a sectional view of the goggle of the second embodiment in which a part with a water cut-off filter pasted is cut vertically.
Figure 8:
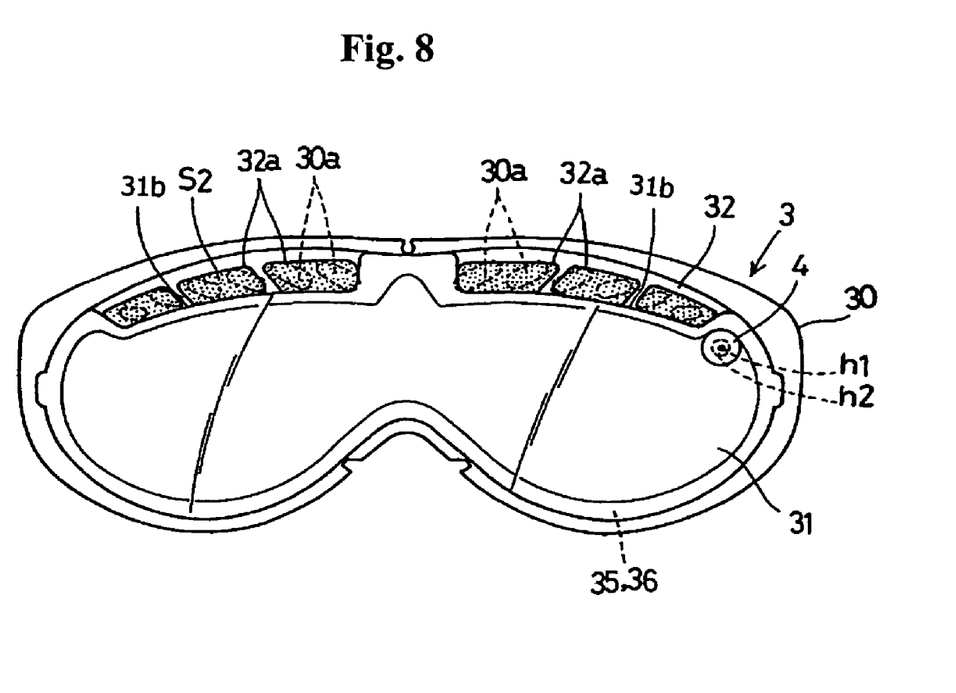
FIG. 8 illustrates a goggle lens used for the goggle of the second embodiment viewed from the inner lens side.

A second embodiment of the optical structure for eyes of the present invention is illustrated in FIGS. 6 to 8.

A ski goggle G has a goggle frame 1, an elastic band 2 linked with the goggle frame 1, a goggle lens 3 composed of three lenses which are detachably fitted in the goggle frame 1 and a water cut-off filter 4.

As shown in FIGS. 6 and 8, the goggle lens 3 of the second embodiment has three lenses; an outer lens 30, a middle lens 32 and an inner lens 31, respectively being of transparent resin. Water cut-off buffer materials 35 and 36 for peripheral sealing are provided between and along the entire circumferential edges of respectively adjacent lenses 30, 32 and 31. The adjacent lenses 30 and 32, 32 and 31, and the water cut-off buffer materials 35 and 36 therebetween are respectively pasted together with double-sided adhesive tapes. The outer and middle lenses 30 and 32 are disposed in parallel separately by 2 mm distance and so the middle and the inner lenses 32 and 31 are. The former define a front room R1 and the latter define a rear room R2. The rooms R1 and R2 respectively function as adiabatic layers. The outer, middle and inner lenses 30, 32 and 31 respectively have a thickness of about 0.6 mm and have a convex shape in which a center portion protrudes from end portions.

As shown in FIGS. 6 and 8, the outer lens 30 is larger in size than the other two lenses 32 and 31 and has holes 30a for a ventilation portion 3a near its upper edge. And its outer peripheral rim is a portion to be fitted into a lens fitting rim 10 of the goggle frame 1. The middle lens 32 is a little smaller in size than the outer lens 30 and has holes 32a for the ventilation portion 3a near its upper edge. The inner lens 31 has a shape with two dent portions 31b at its upper rim portion corresponding to the foregoing ventilation portion 3a.

The outer lens 30 has an ultraviolet absorption function or an ultraviolet reflection function for cutting most of ultraviolet rays and a hard coat 8 on its front face. On the front faces of the middle and inner lenses 32 and 31 are respectively provided a metal film (an inorganic films) 5 of such as silver or chromium. This makes the film 5 a mirror film viewed from a bright side and semi-transparent viewed from a dark side. Further, an antifogging film 7 is added on the rear face of the inner lens 31, the rear face being to confront a wearer's face.

Between the outer and middle lenses 30 and 32 is a sponge plate S2 provided at a portion corresponding to the dent portions 31b for the same reason why the sponge plate S1 is provided.

In the goggle lens 3, as shown in FIGS. 7 and 8, the middle lens 32 has a pressure adjusting hole h1 at a portion near its outer edge and off a wearer's visual field and the inner lens 31 has another pressure adjusting hole h2 at a portion corresponding to the pressure adjusting hole h1. As clearly shown in FIG. 7, the pressure adjusting hole h2 is covered with a water cut-off filter 4.

As the cut-off filter 4, the type of filter similar to the first embodiment is employed. When atmospheric pressure is changed while downhill skiing and the like, the pressures of the inside and outside of the goggle lens 3 are equalized through the water cut-off filter 4. This prevents deformation of the outer, middle and inner lenses 30, 32 and 31 and distortion of visual field.

When external atmospheric pressure increases, external air is sucked in from the pressure adjusting hole h2 through a water repellent permeation sheet (the water cut-off filer). However similar to the first embodiment, fog is not generated inside of the goggle lens 3.

The benefits of this goggle is as follows.

(1) The metal film 5, or the inorganic film, is applied on the front face of the middle lens 32 and the front face of the inner lens 31. Namely, the inorganic film does not exist on the front face of the outer lens 30 which is likely to have external contacts with flying articles, wiping scratches and damage when a wearer falls down. Therefore, the inorganic film of this goggle does not peel off by external factors.

(2) The outer lens 30 has an ultraviolet absorption function or an ultraviolet reflection function for cutting most of ultraviolet rays, and therefore the metal films 5 (i.e. the inorganic films) on the front faces of the middle and inner lenses 32 and 31 are not exposed to ultraviolet rays. As a result, the inorganic films of the goggle do not peel off by external factors.

(3) The metal films 5, or the inorganic films, are applied on the front faces of the middle and inner lenses 32 and 31. The water cut-off filter 4 prevents snow and moisture such as rain from invading into the front room defined by the rear face of the outer lens 30 and the front face of the middle lens 32 and the rear room defined by the rear face of the middle lens 32 and the front face of the inner lens 32. The inorganic films are not directly exposed to moisture, and therefore they do not peel off by moisture.

Some modifications of the second embodiment, which have the basic structure as a goggle similar to the second embodiment, are described below.

(1) The antireflection films 6, or the inorganic films, may be applied on the rear face of the outer lens 30 and the rear face of the middle lens 32 of the above second embodiment. The antireflection films 6, or the inorganic films, do not peel off by external factors.

(2) The outer lens 30 of the second embodiment may be an ultraviolet absorbing polarized lens.

(3) Different from the second embodiment, the metal films 5, or the inorganic films, may be applied on the rear faces of the outer and middle lenses 30 and 32, not on the front faces of the middle and inner lenses 32 and 31.

What is claimed is:

1. An optical structure for eyes comprising:
   plural bent lens members respectively having front and rear faces, which are concave or convex, and being disposed in parallel, the front faces facing away from a wearer's face and the rear faces facing the wearer's face;
   a peripheral sealing between and along entire circumferential edges and/or their surroundings of respective adjacent lens members to form a room between the lens members;
   an inorganic film being applied on at least one of faces defining the room; and
   wherein the inorganic film is applied at least on one of the convex faces and is selected from a metal film, a metal oxide film containing silicon and a metal nitride film containing silicon, wherein
   the plural lens members are an outer lens positioned away from a wearer's face and an inner lens positioned near the wearer's face,
   the peripheral sealing is provided between and along the entire circumferential edges and/or their surroundings of the outer and inner lenses to form the room therebetween, and
   the inorganic film is provided at least on a front face of the inner lens.

2. An optical structure for eyes according to claim 1, wherein an inorganic film is provided on the rear face of the outer lens and is an antireflection film.

3. An optical structure for eye according to claim 2, wherein at least the outer lens has an ultraviolet absorption function or an ultraviolet reflecting function.

4. An optical structure for eyes according to claim 2, wherein the rear face of the inner lens is provided with an antifogging film.

5. An optical structure for eyes according to claim 2, wherein a pressure adjusting hole is provided in at least one of the outer lens, the inner lens and the sealing not to generate difference between the room pressure and exterior pressure.

6. An optical structure for eye according to claim 1, wherein at least the outer lens has an ultraviolet absorption function or an ultraviolet reflecting function.

7. An optical structure for eyes according to claim 6, wherein the rear face of the inner lens is provided with an antifogging film.

8. An optical structure for eyes according to claim 6, wherein a pressure adjusting hole is provided in at least one of the outer lens, the inner lens and the sealing not to generate difference between the room pressure and exterior pressure.

9. An optical structure for eyes according to claim 1, wherein the rear face of the inner lens is provided with an antifogging film.

10. An optical structure for eyes according to claim 1, wherein a pressure adjusting hole is provided in at least one of the outer lens, the inner lens and the sealing not to generate difference between the room pressure and exterior pressure.

11. An optical structure for eyes according to claim 10, wherein an inorganic film is provided on the rear face of the outer lens and is an antireflection film.

12. An optical structure for eye according to claim 11, wherein at least the outer lens has an ultraviolet absorption function or an ultraviolet reflecting function.

13. An optical structure for eyes according to claim 11, wherein the rear face of the inner lens is provided with an antifogging film.

14. An optical structure for eyes according to claim 11, wherein a pressure adjusting hole is provided in at least one of the outer lens, the inner lens and the sealing not to generate difference between the room pressure and exterior pressure.

15. An optical structure for eye according to claim 10, wherein at least the outer lens has an ultraviolet absorption function or an ultraviolet reflecting function.

16. An optical structure for eyes according to claim 10, wherein the pressure adjusting hole is covered with a waterproof filter with air permeability.

17. An optical structure for eye according to claim 1, wherein the plural lens members further comprise a middle lens positioned between the outer and inner lenses, the peripheral sealing is provided between and along the entire circumferential edges and/or their surroundings of the outer and middle lenses to form a front room section therebetween, and between and along the entire circumferential edges and/or their surroundings of the middle and inner lenses to form a rear room section therebetween, the front and rear room sections compose the room, and the inorganic film is provided on at least one of a front face of the middle lens and a front face of the inner lens.

18. An optical structure for eyes according to claim 17, wherein the inorganic film on the front face of the middle lens is selected from a metal film, a metal oxide film containing silicon and a metal nitride film containing silicon.

19. An optical structure for eyes according to claim 18, wherein an inorganic film is provided on the rear face of the outer lens and/or the rear face of the middle lens and is an antireflection film.

20. An optical structure for eye according to claim 19, wherein at least the outer lens has an ultraviolet absorption function or an ultraviolet reflecting function.

21. An optical structure for eyes according to claim 19, wherein a hard coat is applied on the front face of the outer lens.

22. An optical structure for eyes according to claim 19, wherein the rear face of the inner lens is provided with an antifogging film.

23. An optical structure for eyes according to claim 19, wherein a pressure adjusting hole is provided in at least one of the outer lens, the middle lens, the inner lens and the sealing not to generate difference between the room pressure and exterior pressure.

24. An optical structure for eye according to claim 18, wherein at least the outer lens has an ultraviolet absorption function or an ultraviolet reflecting function.

25. An optical structure for eyes according to claim 18, wherein a hard coat is applied on the front face of the outer lens.

26. An optical structure for eyes according to claim 18, wherein the rear face of the inner lens is provided with an antifogging film.

27. An optical structure for eyes according to claim 18, wherein a pressure adjusting hole is provided in at least one of the outer lens, the middle lens, the inner lens and the sealing not to generate difference between the room pressure and exterior pressure.

28. An optical structure for eyes according to claim 17, wherein an inorganic film is provided on the rear face of the outer lens and/or the rear face of the middle lens and is an antireflection film.

29. An optical structure for eye according to claim 28, wherein at least the outer lens has an ultraviolet absorption function or an ultraviolet reflecting function.

30. An optical structure for eyes according to claim 28, wherein a hard coat is applied on the front face of the outer lens.

31. An optical structure for eyes according to claim 28, wherein the rear face of the inner lens is provided with an antifogging film.

32. An optical structure for eyes according to claim 28, wherein a pressure adjusting hole is provided in at least one of the outer lens, the middle lens, the inner lens and the sealing not to generate difference between the room pressure and exterior. pressure.

33. An optical structure for eye according to claim 17, wherein at least the outer lens has an ultraviolet absorption function or an ultraviolet reflecting function.

34. An optical structure for eyes according to claim 17, wherein a hard coat is applied on the front face of the outer lens.

35. An optical structure for eyes according to claim 17, wherein the rear face of the inner lens is provided with an antifogging film.

36. An optical structure for eyes according to claim 17, wherein a pressure adjusting hole is provided in at least one of the outer lens, the middle lens, the inner lens and the sealing not to generate difference between the room pressure and exterior pressure.

37. An optical structure for eyes according to claim 36, wherein the pressure adjusting hole is covered with a waterproof filter with air permeability.

38. An optical structure for eyes according to claim 17, where the peripheral sealing is made of water cut-off buffer material.

39. An optical structure for eyes according to claim 1, where the peripheral sealing is made of water cut-off buffer material.

* * * * *